(12) United States Patent
Kelly et al.

(10) Patent No.: US 9,370,191 B2
(45) Date of Patent: Jun. 21, 2016

(54) COSMETIC FORMULATION

(71) Applicants: Pardis Kelly, San Carlos, CA (US); Stefanie Grotkin, Pacifica, CA (US)

(72) Inventors: Pardis Kelly, San Carlos, CA (US); Stefanie Grotkin, Pacifica, CA (US)

(73) Assignees: Pardis Kelly, San Carlos, CA (US); Stefanie Grotkin, Pacifica, CA (US)

( * ) Notice: Subject to any disclaimer, the term of this patent is extended or adjusted under 35 U.S.C. 154(b) by 0 days.

(21) Appl. No.: 13/959,704

(22) Filed: Aug. 5, 2013

(65) Prior Publication Data

US 2014/0044657 A1 Feb. 13, 2014

Related U.S. Application Data

(60) Provisional application No. 61/680,395, filed on Aug. 7, 2012.

(51) Int. Cl.
| | |
|---|---|
| *A61K 8/96* | (2006.01) |
| *A01N 65/36* | (2009.01) |
| *A61Q 3/02* | (2006.01) |
| *A01N 65/00* | (2009.01) |
| *A61Q 17/00* | (2006.01) |
| *A61K 8/97* | (2006.01) |

(52) U.S. Cl.
CPC ............. *A01N 65/36* (2013.01); *A01N 65/00* (2013.01); *A61K 8/96* (2013.01); *A61K 8/97* (2013.01); *A61Q 3/02* (2013.01); *A61Q 17/005* (2013.01)

(58) Field of Classification Search
CPC ... A61K 2300/00; A61K 8/731; A61K 31/17; A61K 31/4174; A61K 31/60; A61K 33/04; A61K 36/185; A61K 36/48; A61K 36/899; A61K 8/8152; A61K 2800/594; A61K 8/8158; A61K 8/8164; A61K 8/84; A61K 8/08
See application file for complete search history.

(56) References Cited

U.S. PATENT DOCUMENTS

| | | | |
|---|---|---|---|
| 4,179,304 A | 12/1979 | Rossomando | |
| 5,130,125 A | 7/1992 | Martin et al. | |
| 5,290,543 A * | 3/1994 | Ounanian et al. | 424/61 |
| 5,639,447 A | 6/1997 | Patel | |
| 5,766,332 A * | 6/1998 | Graves et al. | 106/169.17 |
| 6,537,530 B2 | 3/2003 | Mui et al. | |
| 7,074,392 B1 * | 7/2006 | Friedman et al. | 424/61 |
| 8,128,919 B2 | 3/2012 | Fleissman et al. | |
| 2010/0074854 A1 * | 3/2010 | Guerchet et al. | 424/61 |
| 2012/0128619 A1 | 5/2012 | Knappe et al. | |

OTHER PUBLICATIONS

"Research Update: Grapefruit Seed Extract", MD idea Exporting Division, published online Apr. 12, 2011. Accessed online at http://www.mdidea.com/products/new/new010research.html on Jan. 5, 2015.*

Baran et al. "Nail fragility syndrome and its treatment", Journal of Cosmetic Dermatology, Jul. 2004, vol. 3, Issue 3, p. 131-137.*

Ignacio and Thai, "Comparative Analysis of Antifungal Activity of Natural Remedies Versus Miconazole Nitrate Salt Against *Candida albicans*", Biological Sciences Dept., California Polytechnic State University, 2005, pp. 1-25.

* cited by examiner

*Primary Examiner* — Audrea Buckley
(74) *Attorney, Agent, or Firm* — Convergent Law Group LLP

(57) ABSTRACT

The present invention relates generally to nail polish formulations for application to natural or artificial finger- or toenails, where the nail polish formulation comprises grapefruit seed extract that imparts antifungal and other antimicrobial properties.

20 Claims, No Drawings

COSMETIC FORMULATION

RELATED APPLICATIONS

This application claims priority to U.S. Ser. No. 61/680,395, filed 7 Aug. 2012.

FIELD OF THE INVENTION

The present invention relates generally to nail polish formulations for application to natural or artificial finger- or toenails, where the nail polish formulation comprises grapefruit seed extract that imparts nourishing, antifungal and other antimicrobial properties to the nail.

BACKGROUND OF THE INVENTION

In the following discussion, certain devices and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Numerous types of liquid nail polish formulations are sold commercially. Liquid nail polish formulations typically contain a film former such as nitrocellulose, which makes the polish waterproof, tough and hard; a plasticizer such as various resins, camphor, and phthalates to provide flexibility; solvents and diluents that are usually a blend of low, medium and high boiling point liquids such as acetone, ethyl acetate, n-butyl acetate, and ethanol; pigments and other compounds to impart color, and, e.g., opacity, gloss, or metallic qualities; and thixotropic compounds, anti-oxidants, UV-stabilizers, and the like to improve qualities of the polish to optimize shelf-life, flow, homogeneity, and color consistency and to prevent sedimentation and separation. However, most polishes do not additionally comprise ingredients that are good for the nails.

Onychomycosis is a fungal disease of the nail. It is the most common disease of the nails and constitutes about half of all nail abnormalities. The condition may affect toenails or fingernails, but toenail infections are particularly common. The prevalence of onychomycosis is about 6-10% in the adult population.

What is needed in the art is a nail polish formulation that provides a glossy, fashionable, attractive and durable nail polish while treating or retarding onychomycosis and/or imparting other antimicrobial or health benefits to the nails. The present invention meets this unmet need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Thus, in one embodiment there is provided an antimicrobial nail polish composition comprising: grapefruit seed extract (GSE); one or more film-forming components; one or more solvents and/or diluents; one or more plasticizers; and one or more thixotropic agents. In some formulations of this embodiment, the GSE is at a concentration of from about 0.05% to about 1.0% (w/w) of the nail polish composition and in other formulations of this embodiment, the GSE is at a concentration of from about 0.05% to about 0.50% (w/w) or about 0.15% to about 0.25%, or about 0.05% to about 0.15%, or about 0.05% to 0.25%, or about 0.05% to 0.35%, or about 0.10% to about 0.25%, or about 0.10% to about 0.30% or about 0.10% to about 0.40%, or about 0.20% to about 0.30%, or about 0.20 to about 0.40%, or about 0.20 to about 0.50%, or about 0.25% to about 0.50%, or about 0.25 to about 0.40%, or about 0.25 to about 0.35%, or about 0.05% to about 0.10% (w/w) of the nail polish composition. In yet other formulations of this embodiment, the one or more film-forming components are selected from the group of nitrocelluloses, celluloses, vinyl polymers, ether urethanes, acetates, or polyester resins, and in preferred formulations of this embodiment, the one or more film-forming components are selected from ECOCELL™ ½ ES (nitrocellulose/isopropyl alcohol (RS ½ sec)) or ECOCELL™ ¼ ES (nitrocellulose/isopropyl alcohol (RS ¼ sec)), NX-55 (sulfonamide resin) or sucrose acetate isobutyrate.

In some formulations, the one or more plasticizers are selected from the group of castor oil, camphor, butyl glycolate, butyl stearate, triethyl citrate, dibutyl tartrate, benzyl benzoate, butyl acetyl ricinoleate, diethyl adipate, dibutyl adipate, diisobutyl adipate, dihexyl adipate, dicapryl adipate, di(2 ethyylhexyl) adipate, diisooctyl adipate, dinonyl adipate, octyl decyl adipate, isooctyl isodecyl adipate, polypropylene glycol adipate, dimethoxyethyl adipate, diethoxyethyl adipate, dibutoxyethyl adipate, dimethyl phthalate, diethyl phthalate, dipropyl phthalate, dibutyl phthalate, diisobutyl phthalate, butyl octyl phthalate, butyl isodecyl phthalate, butyl isohexyl phthalate, auryl isohexyl phthalate, dioctyl terephthalate, diisooctyl phthalate, dicaprul phthalate, di(2-ethylhexyl) phthalate, dinomyl phthalate, diethyl decyl phthalate, iso-octyl isodecyl phthalate, dodecyl phthalate, ethylhexyldecyl phthalate, butyl ethylhexyl phthalate, 2-ethlhexyl diphenyl phosphate, modified tiraryl phosphate ester, triphenyl phosphate, 2-hydroxy-4-methoxybenzophenone, non-ethyl-p-toluenesulfonamide, tricresyl phosphate, Lexorez® (polyol esterpolymer), or Lexfilm® (neopentyl glycol diheptanoate), and in preferred formulations, the one or more plasticizers is Lexorez® (polyol esterpolymer), Lexfilm® (neopentyl glycol diheptanoate), triphenyl phosphate, or dioctyl terephthalate.

Preferred embodiments of the formulation comprise the thixotropic agent stearalkonium hectorite; and in even more preferred embodiments, the stearalkonium hectorite is Bentone 27V (stearalkonium hectorite rheological additive).

Some embodiments of the formulation further comprise one or more pigments. In preferred embodiments, the pigment is formulated with nitrocellulose.

Preferred embodiments of the formulation also comprise one or more of an anti-oxidant, a UV-stabilizer or a nail plate hardener. In preferred embodiments, the anti-oxidant is citric acid, the UV-stabilizer is benzephenone 3, and the nail plate hardener is N-N'-dimethylurea, which also serves as a vehicle to allow the penetration of GSE into the nail. In yet other embodiments, the formulation further comprises polydimethicone as a feel agent.

DETAILED DESCRIPTION OF THE INVENTION

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The practice of the techniques described herein may employ, unless otherwise indicated, conventional techniques and descriptions of chemical cosmetic formulation, all of which are within the skill of those who practice in the art. Specific illustrations of suitable techniques can be had by reference to the Examples herein; however, other equivalent conventional procedures can, of course, also be used. Such conventional techniques and descriptions can be found in standard manuals and texts such as Romanowski and Schueller, *Beginning Cosmetic Chemistry*, 3d Ed. (Allured Pub Corp, 2009), Michalun, *Milady's Skin Care and Cosmetic Ingredients*, 3d Ed. (Milady, 2009); Schlossman, *Chemistry and Manufacture of Cosmetics: Science, Vols.* 1 and 2, 4$^{th}$ Ed. (Allured Pub Corp., 2008); Barel, et al., Eds., *Handbook of Cosmetic Science and Technology*, 3d Ed., (INFRMA-HC 2009); and O'Lenick and O'Lenick, *Organic Chemistry for Cosmetic Chemists* (Allured Pub Corp., 2008). US patents and published applications include U.S. Pat. Nos. 8,128,919; 6,537,530; 6,106,820; 5,882,636; 5,747,018; 5,720,804; 5,639,447; 5,346,652; 5,130,125; 4,749,564; and 4,179,304; and US Pub. Nos. 2012/0138076; 2012/0128619; 2012/0041589; 2011/0226803; 2010/0099841; 2007/0189995; and 2005/0220730. All references, patent documents and other art cited herein are hereby incorporated in their entirety by reference for all purposes.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any intervening value in that stated range is encompassed within the invention. The upper and lower limits of these smaller ranges may independently be included in the smaller ranges, and are also encompassed within the invention subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention.

There are a number of desirable properties that nail polish should possess.

In particular, the nail polish formulations of the present invention dry and harden quickly, apply easily, are adherent yet flexible, glossy, waterproof and suitably colored, wear well, e.g., resist chipping, peeling and abrasion and are dermatologically innocuous. However, in addition to these properties, the nail polish formulations of the present invention also are good for the nails, as the present formulations treat and/or retard onychomycosis, the condition of fungal infection of the nail as well as provide other antimicrobial properties and further health benefits. Specifically, the antifungal nail polish formulations of the present invention comprise a natural compound, grapefruit seed extract (GSE).

GSE is a liquid derived from the seeds, pulp, and white membranes of grapefruit. Self-made natural GSE processed in the laboratory without solvents or synthetic agents is prepared by grinding the grapefruit seed and juiceless pulp, then typically mixing this "paste" with glycerin. Commercially-available GSE is made from the seed and pulp of the grapefruit, glycerin, and, optionally, synthetic preservatives blended together. Grapefruit seed extract is sold as a food supplement because it is a natural antimicrobial (antibacterial, antiviral, and antifungal) and has been used in cosmetics such as lotion, but has never been included in a nail polish formulation until the present invention. GSE has also been reported as being a safe, natural, and effective preservative.

The GSE-containing, antifungal nail polish formulations of the present invention can be formulated as a clear, colorless lacquer composition, or optionally mixed with a pigment component when a colored polish is desired. GSE is present in the formulations of the present invention at approximately 0.05% to 1.00% (w/w), 0.10% to 0.8%, 0.10% to 0.75%, 0.10% to 0.65%, or more preferably at 0.05% to 0.25% (w/w), or even more preferably at 0.055% to 0.15% (w/w). GSE is available commercially through NutriBiotic (Lakeport, Calif.). In addition, GSE has been reported to have antibacterial properties (see, e.g., Heggers, et al., J. Altern. Complement Med., 8(3):333-40 (2002)), preservative properties, as well as specific antifungal properties against *Candida albicans* (see, C. Ignacio and D. Thai, "Comparative Analysis of Antifungal Activity of Natural Remedies versus Miconazole Nitrate Salt Against *Candida albicans*", available at the Cal Poly senior projects website.

The film-forming component of the antifungal nail polish formulation in preferred embodiments comprises nitrocellulose, selected for its hardness, toughness, resistance to abrasion and ability to release solvent rapidly. Nitrocelluloses are readily available commercially and have varying viscosity grades, such as SS/2 or RS ¼ sec. The RS ¼ sec. grade has a high solids content. Other useful viscosity grades include RS ½ sec. which has a high non-volatile content. Nitrocelluloses that have a nitrogen content of about 10.2% to about 12.8% and are soluble in esters, ketones and glycol ethers are preferred. Nitrocellulose is available from many manufacturers, including Hercules, Inc., Wilmington, Del. The terms ¼ sec. and ½ sec., etc. represent measurement of viscosity (based on the length of the polymer) and refers to the time it takes for a ball to fall to a given depth in the material. Ecocell™ ½ ES or Ecocell™ ¼ ES nitrocelluloses or a combination thereof are presently preferred. The amount of the film-forming component is chosen to produce a hardened coating thickness of about 0.0001 inch to 0.0005 inch.

Other film-forming components, like the nitrocellulose, are chosen on the basis of their ability to build the film and to enhance the depth, gloss and adhesion of the applied polish. Useful film formers include but are not limited to celluloses such as ethyl cellulose, cellulose acetate, and cellulose acetate-butyrate; vinyl polymers such as polyvinyl acetate, and polyvinyl butyrate; ether urethanes such as polyurethane resins; and polyester resins formed from monomers ethyl acrylate and ethyl methylacrylate. Preferred film formers include sucrose acetate isobutyrate and a tosylamide epoxy resin such as NX-55 supplied by Estron Co., Calvert City, Ky. Preferably, sucrose acetate isobutyrate and NX-55 in an amount of about 5% to about 20% (w/w) is employed. Other polyester resins that may be employed are 2,2,4-trimethyl-1, 3-pentanediol, isophthalic acid-85, and trimellitic anhydride and mixtures thereof.

There are a number of different solvents and/or diluents that can be used in the present invention, including but not limited to ethyl acetate, isobutyl acetate, butyl acetate, xylene, toluene, heptane, and mixtures of lower alkyl acetates, lower alcohols (ethanol, isopropyl alcohol or butyl alcohol), and lower alkyl ketones. Solvents suitable for use typically include ethyl acetate with at least one of isobutyl acetate and propylene glycol monomethyl ether acetate (PM acetate). The solvent system includes about 10% to about 50% (w/w) ethyl acetate, or about 15% to about 35% (w/w) ethyl acetate, and preferably about 20% to about 40% (w/w) ethyl acetate; and about 15% to about 35% (w/w) N-butyl acetate, or about 15% to about 32% (w/w) N-butyl acetate, and preferably about 20% to about 30% (w/w) N-butyl acetate; and about 0% to about 10% (w/w) PM acetate, or about 2% to about 8% (w/w) PM acetate, and preferably about 2% to about 5% (w/w) PM acetate; and about 0% to about 10% (w/w) ethanol, and preferably about 3% to about 8% (w/w) ethanol; and about 0% to about 8% (w/w) isopropyl alcohol, and preferably about 3% to about 8% (w/w) isopropyl alcohol.

Plasticizers are included to impart flexibility to the nail polish formulation. The choice of plasticizer may vary as a function of the effect on viscosity of the polish, effect on the drying rate, the amount needed to meet flexibility requirements, the volatility of the plasticizer, as well as compatibility with the other components of the polish composition. Plasticizers that may be used in the lacquer component include but are not limited to castor oil, camphor, butyl glycolate, butyl stearate, triethyl citrate, dibutyl tartrate, benzyl benzoate, butyl acetyl ricinoleate, diethyl adipate, dibutyl adipate, diisobutyl adipate, dihexyl adipate, dicapryl adipate, di(2 ethyylhexyl)adipate, diisooctyl adipate, dinonyl adipate, octyl decyl adipate, isooctyl isodecyl adipate, polypropylene glycol adipate, dimethoxyethyl adipate, diethoxyethyl adipate, dibutoxyethyl adipate, dimethyl phthalate, diethyl phthalate, dipropyl phthalate, dibutyl phthalate, diisobutyl phthalate, butyl octyl phthalate, butyl isodecyl phthalate, butyl isohexyl phthalate, auryl isohexyl phthalate, dioctyl terephthalate, diisooctyl phthalate, dicaprul phthalate, di(2-ethylhexyl)phthalate, dinomyl phthalate, diethyl decyl phthalate, iso-octyl isodecyl phthalate, dodecyl phthalate, ethylhexyldecyl phthalate, butyl ethylhexyl phthalate, 2-ethlhexyl diphenyl phosphate, modified tiraryl phosphate ester, triphenyl phosphate, 2-hydroxy-4-methoxybenzophenone, No-ethyl-p-toluenesulfonamide, tricresyl phosphate (all of which are available from a number of manufacturers) or Lexorez® or Lexfilm® compounds (available from Inolex Chemical Co., Philadelphia, Pa.). Preferably, dioctyl terephthalate or triphenyl phosphate or a combination thereof is employed in the lacquer component in an amount of about 0% to about 40% (w/w), or about 1% to about 35% (w/w), or about 5% to about 30% (w/w), preferably about 5% to about 25% (w/w), and most preferably about 7% to about 15% (w/w) of the nail polish formulation.

An "anti-settling" or thixotropic agent is also present in the nail polish formulation in an amount effective to gel the composition. Thixotropic agents are agents that impart a quality to fluid where such fluids are thick or viscous under normal conditions but flow when shaken or otherwise agitated. Useful thixotropic agents include but are not limited to stearalkonium hectorites such as Bentone™ 27V, supplied by Elementic Specialities, Inc., East Windsor, N.J. Typically, the thixotropic agent is present in an amount of about 0.5 to about 3.0% (w/w).

In preferred aspects of the invention, pigment is included in the nail polish formulation to provide colored nail polish formulations. Useful pigments include but are not limited to D&C pigments (such as D&C Red #6 Barium Lake, D&C Red #7 Calcium Lake, D&C Red #34 Calcium Lake, D&C Red #17, D&C Red #33, D&C Violet #2, D&C Yellow #11), FD&C pigments (such as FD&C Yellow #5 Aluminum Lake, FD&C Blue #1 and FD&C Green #3); titanium dioxide, ferric ferrocyanide mica, iron oxides, iron black aluminum silicate and iron blue aluminum silicate; and pigments pre-formulated with nitrocellulose and/or plasticizers. In addition to the above-named pigments, irridescent additives such as opalescence or pearl essence—a suspension of crystalline guanine in nitrocellulose and solvents—may be employed. The amount of pigment in the overall formulation may be about 0.5% to about 5% (w/w), or about 1.0% to about 4.0% (w/w), or about 1.0% to about 3.0% (w/w), or about 1.0% to about 2.5% (w.w), and preferably about 1.0% to about 2.0% (w/w).

In addition to the above-listed components, the nail polish formulation may further comprise brightening agents, UV-stabilizers, anti-oxidants, drying accelerators and the like. Useful brightening agents include bismuth oxychloride and hydrated alumina. Benzephenone 3 may be added to the formulation and act as both a drying accelerator and a UV-stabilizer (which aids in preventing yellowing of the nail), and citric acid is an effective anti-oxidant. Additionally, one or more of a nail plate hardener such as N,N' Dimethylurea which in addition serves as a vehicle to allow penetration of the GSE into the nail, and a feel agent such as polydimethicone (e,.g, an agent to prevent chipping and marring and to impart additional gloss) may be employed.

Generally, in forming a nail polish formulation, the components of the formulation may be blended with any of a series of ingredients to enhance or impart various properties. In one specific, exemplary embodiment, the compounds in Table 1 were blended in the following way:

First, n-butyl acetate and stearalkonium hectorite were added into a sealed mixing vessel and mixed until smooth with a silica media. The stearalkonium hectorite was activated by adding ethanol and increasing the agitation until a paste was formed. At this stage, the ethyl acetate, PM acetate (1-Methoxy-2-Propanol Acetate), isopropanol and citric acid were added. Next, the nitrocellulose and nitrocellulose chips were added under increasing agitation. The agitation was increased until the mixture was fully involved and continued until the mixture was completely homogenous. The triphenyl phosphate, dioctyl terephthalate, tosyl-amide epoxy and sucrose acetate isobutyrate were then added. Stirring was continued and the mixture was allowed to sweat for approximately 30 to 45 minutes until the consistency of the mixture was consistent. During the blending process, the temperature was not allowed to exceed 130° F. The GSE, N,N' Dimethylurea, polydimethicone and benzephenone were then added and the final mixture was stirred for 15 to 20 additional minutes. Finally, the mixture was allowed to return to ambient temperature and allowed to swell for 12 to 24 hours. At this point, the percent solids, viscosity or other parameters of the formulation may be checked versus specifications for the final formulation, and adjustments may be made, e.g., with a solvent blend. Typically, the formulations used a 3:1 weight ratio of nitrocellulose to polyester resin; however the range of ratios of 9:1 to 2:1 or preferably 5:1 to 2.5:1 may be employed.

The GSE was tested for compatibility with several polyester resins. The resins were mixed with 1% or 5% GSE, and no precipitation and phase separation was noted with any of the film forming compounds tested.

TABLE 1

Preferred Formulation

| Chemical Name | Function | Range (% w/w) | Preferred (% w/w) |
|---|---|---|---|
| Ethyl acetate | Solvent | 20-40 | 27.39 |
| N-Butyl acetate | Solvent | 20-30 | 28.99 |
| PM acetate | Solvent | 0-10 | 2.32 |
| Ethanol | Solvent | 3-8 | 5.3 |
| Isopropanol | Solvent | 3-8 | 6.05 |
| Citric acid | Anti-Oxidant | 0.01-0.05 | 0.02 |
| Stearalkonium hectorite | Thixotropic agent | 0.5-3 | 0.84 |
| Nitrocellulose pigment chips | Pigment | 0.5-5 | 1.28 |
| GSE | Antimicrobial | 0.05-0.50 | 0.05 |
| NN'Dimethylurea | Nail plate Modifier | 0.05-0.20 | 0.09 |
| Polydimethicone | Feel agent | 0.03-0.10 | 0.05 |
| Triphenyl phosphate | Plasticizer | 0-10 | 4.64 |
| Dioctyl terephthalate | Plasticizer | 0-10 | 3.1 |
| Nitrocellulose | Resin | 0-15 | 14.07 |
| Tosyl-amide expoy | Resin | 0-5 | 2.9 |
| Sucrose acetate isobutyrate | Resin | 0-5 | 2.79 |
| Benzephenone 3 | UV-stabilizer | 0.05-0.20 | 0.12 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. §112, ¶6.

We claim:

1. An antimicrobial nail polish composition comprising:
   a glycerin-based grapefruit seed extract (GSE) formulation, wherein the GSE is at a concentration of from 0.05% to 0.50% (w/w) of the nail polish composition;
   one or more film-forming components;
   one or more solvents and/or diluents;
   one or more plasticizers;
   and one or more thixotropic agent, wherein said antimicrobial nail polish composition is adherent yet flexible, glossy, resists chipping and treats and/or retards onychomycosis.

2. The antimicrobial nail polish of claim 1, wherein the GSE is at a concentration of from 0.05% to 0.15% (w/w) of the nail polish composition.

3. The antimicrobial nail polish of claim 2, wherein the GSE is at a concentration of from 0.05% to 0.10% (w/w) of the nail polish composition.

4. The nail polish composition of claim 1, wherein the one or more film-forming components are selected from the group of nitrocelluloses, celluloses, vinyl polymers, ether urethanes, acetates, or polyester resins.

5. The nail polish composition of claim 4, wherein the one or more film-forming components are selected from Ecocell™ ½ ES (nitrocellulose/isopropyl alcohol (RS ½ sec)) or Ecocell™ ¼ ES (nitrocellulose/isopropyl alcohol (RS ¼ sec)), NX-55 (sulfonamide resin) or sucrose acetate isobutyrate.

6. The nail polish composition of claim 1, wherein the one or more plasticizers are selected from the group of castor oil, camphor, butyl glycolate, butyl stearate, triethyl citrate, dibutyl tartrate, benzyl benzoate, butyl acetyl ricinoleate, diethyl adipate, dibutyl adipate, diisobutyl adipate, dihexyl adipate, dicapryl adipate, di(2-ethyylhexyl) adipate, diisooctyl adipate, dinonyl adipate, octyl decyl adipate, isooctyl isodecyl adipate, polypropylene glycol adipate, dimethoxyethyl adipate, diethoxyethyl adipate, dibutoxyethyl adipate, dimethyl phthalate, diethyl phthalate, dipropyl phthalate, dibutyl phthalate, diisobutyl phthalate, butyl octyl phthalate, butyl isodecyl phthalate, butyl isohexyl phthalate, auryl isohexyl phthalate, dioctyl terephthalate, diisooctyl phthalate, dicaprul phthalate, di(2-ethylhexyl) phthalate, dinomyl phthalate, diethyl decyl phthalate, iso-octyl isodecyl phthalate, dodecyl phthalate, ethylhexyldecyl phthalate, butyl ethylhexyl phthalate, 2-ethlhexyl diphenyl phosphate, modified tiraryl phosphate ester, triphenyl phosphate, 2-hydroxy-4-methoxybenzophenone, non-ethyl-p-toluenesulfonamide, tricresyl phosphate, Lexorez® (polyol esterpolymer), or Lexfilm® (neopentyl glycol diheptanoate).

7. The nail polish formulation of claim 6, wherein the one or more plasticizers is Lexorez® (polyol esterpolymer), Lexfilm® (neopentyl glycol diheptanoate), triphenyl phosphate, or dioctyl terephthalate.

8. The nail polish formulation of claim 1, wherein the one or more thixotropic agent is a stearalkonium hectorite.

9. The nail polish formulation of claim 8, wherein the stearalkonium hectorite is Bentone 27V (stearalkonium hectorite rheological additive).

10. The nail polish formulation of claim 1, further comprising one or more pigments.

11. The nail polish formulation of claim 10, wherein the pigment is formulated with nitrocellulose.

12. The nail polish formulation of claim 1, further comprising an anti-oxidant.

13. The nail polish formulation of claim 1, further comprising a UV-stabilizer.

14. The nail polish formulation of claim 1, further comprising N-N'-dimethylurea.

15. The nail polish formulation of claim 1, further comprising polydimethicone.

16. An antimicrobial nail polish composition comprising:
   0.05% to 0.50% (w/w) a glycerin-based grapefruit seed extract (GSE) formulation;
   one or more film-forming components selected from Ecocell™ ½ ES (nitrocellulose/isopropyl alcohol (RS ½ sec)) or Ecocell™ ¼ ES (nitrocellulose/isopropyl alcohol (RS ¼ sec)), NX-55 or sucrose acetate isobutyrate;
   one or more solvents and/or diluents;
   one or more plasticizers selected from Lexorez® (polyol esterpolymer), Lexfilm® (neopentyl glycol diheptanoate), triphenyl phosphate, or dioctyl terephthalate;
   and one or more thixotropic agent, wherein said antimicrobial nail polish composition is adherent yet flexible, glossy, resists chipping and treats and/or retards onychomycosis.

17. The nail polish formulation of claim 16, further comprising an anti-oxidant.

18. The nail polish formulation of claim 16, further comprising a UV-stabilizer.

19. The nail polish formulation of claim 16, further comprising N-N'-dimethylurea.

20. The nail polish formulation of claim 16, further comprising polydimethicone.

\* \* \* \* \*